United States Patent [19]

Huser et al.

[11] Patent Number: 5,312,969
[45] Date of Patent: May 17, 1994

[54] LINEAR DICARBONYLATION OF DIFUNCTIONALIZED BUTENES

[75] Inventors: Marc Huser, Villeurbanne; Sylvain Mutez, Irigny; Robert Perron, Charly, all of France

[73] Assignee: Rhone-Poulenc Chimie, Courbevoie, France

[21] Appl. No.: 884,194

[22] Filed: May 18, 1992

[30] Foreign Application Priority Data

May 17, 1991 [FR] France .................... 91 06188

[51] Int. Cl.$^5$ ............................. C07C 67/38
[52] U.S. Cl. ............................. 560/204; 560/207; 562/517; 562/518; 562/519; 562/520; 562/590; 562/595
[58] Field of Search ............ 560/204, 207; 562/517, 562/518, 519, 520, 590, 595

[56] References Cited

U.S. PATENT DOCUMENTS 4,857,657  8/1989  Denis et al. .................. 560/193
5,081,292  1/1992  Denis et al. .................. 560/204 X

FOREIGN PATENT DOCUMENTS 0347340 11/1989 European Pat. Off. .
0395545 10/1990 European Pat. Off. .

*Primary Examiner*—José G. Dees
*Assistant Examiner*—Vera C. Clarke
*Attorney, Agent, or Firm*—Burns, Doane, Swecker & Mathis

[57] ABSTRACT

Difunctional butenes are linearly dicarbonylated into 3-hexene-1,6-dioic acid or alkyl diesters thereof, well suited for the ultimate production of, e.g., adipic acid, by reacting such difunctional butene with carbon monoxide and, if appropriate, an alcohol, at an elevated temperature under superatmospheric pressure, in the presence of at least one source of hydrogen chloride and a catalytically effective amount of palladium, at least a portion of which palladium being in the zero oxidation state, as well as a quaternary onium chloride of nitrogen or phosphorus, the nitrogen or phosphorus atom being tetracoordinated to carbon atoms, with the proviso that the nitrogen atom may be coordinated to two pentavalent phosphorus atoms.

19 Claims, No Drawings

LINEAR DICARBONYLATION OF DIFUNCTIONALIZED BUTENES

BACKGROUND OF THE INVENTION

1. Field of the Invention

The present invention relates to the linear dicarbonylation of difunctionalized butenes.

By "linear dicarbonylation" is intended the predominant formation of 3-hexene-1,6-dioic acid and/or the dialkyl esters thereof, by reacting carbon monoxide, if appropriate also an alcohol, with at least one butene disubstituted by hydroxyl, alkoxy or acyloxy radicals.

2. Description of the Prior Art

It is known to this art that diesters of 3-hexene-1,6-dioic acid can be hydrogenated into the corresponding diesters of adipic acid, which in turn can be hydrolyzed to produce adipic acid.

3-Hexene-1,6-dioic acid can itself be hydrogenated into adipic acid.

Adipic acid, one of the raw materials for producing nylon 66, is currently synthesized in vast amounts. For this fact alone, any novel process for the preparation of this diacid and/or derivative thereof is of basic interest.

European Patent Application EP-A-0,347,340 (corresponding to U.S. Pat. No. 4,925,973) describes a catalytic process for the preparation of diesters of 3-hexene-1,6-dioic acid by reacting carbon monoxide and an alcohol with at least one butene disubstituted by acyloxy radicals. Such linear dicarbonylation is carried out in the presence of a catalyst based on palladium and on a quaternary onium halide of a Group VB element selected from between nitrogen and phosphorus, said element being tetracoordinated to carbon atoms, with the proviso that the nitrogen may be coordinated to two pentavalent phosphorus atoms, and the halide anion being selected from between the chloride and bromide. Such a process permits conducting the carbonylation under conditions of pressure and temperature which are acceptable on an industrial scale, with an appreciable selectivity for a linear dicarbonylated final product, and wherein the proportions of monocarbonylated product and of branched dicarbonylated compounds are very small.

European Patent Application EP-A-0,395,545 describes a catalytic process for the preparation of 1,6-hexenedioic acid by reacting carbon monoxide and water with at least one butene disubstituted by acyloxy radicals. The linear dicarbonylation is also carried out in the presence of a catalyst based on palladium and on a quaternary onium chloride as indicated above.

Example 8 of this application, carried out using metallic palladium deposited onto charcoal and in the presence of tetrabutylphosphonium chloride, does not provide completely satisfactory results.

European Patent Application EP-A-0,395,546 describes, in particular, a process for the preparation of 3-hexene-1,6-dioic acid by reacting carbon monoxide with 2-butene-1,4-diol and/or 1-butene-3,4-diol.

The linear dicarbonylation is carried out in the presence of a catalyst based on palladium and on a quaternary onium chloride, also as indicated above.

Example 21 of this application, carried out using metallic palladium deposited onto charcoal in the presence of tetrabutylphosphonium chloride, also does not provide completely satisfactory results.

European Patent Applications Nos. 90/322,256, 90/322,257 and 90/322,258 respectively describe replacing the onium halide as defined above, at least partially, by a pair or couple constituted by certain inorganic halides and by a basic aprotic polar solvent.

French Patent Application No. 90/12,042 describes another catalytic process for the preparation of diesters of 3-hexene-1,6-dioic acid by reacting carbon monoxide with a 1,2-dialkoxy-3-butene, either alone or in admixture with a 1,4-dialkoxy-2-butene.

The linear dicarbonylation is carried out in the presence of a catalyst based on palladium and on an ionic chloride in which the cation is selected from among the alkali metal cations, alkaline earth metal cations and quaternary onium cations as defined above.

However, each of the aforedescribed catalytic processes for the linear dicarbonylation of difunctionalized butenes, the fundamental benefits of which are not in dispute, presents at least one of the following disadvantages and drawbacks:

(1) Certain sources of palladium, and in particular metallic palladium deposited on a support, do not exhibit a fully satisfactory activity under certain reaction conditions;

(2) The catalyst system exhibits an insufficient stability with time, manifested by the precipitation of palladium over time on the walls and base of the carbonylation reactor.

Thus, need continues to exist in this art for a catalytic process for the linear dicarbonylation of difunctionalized butenes, in which the palladium-based catalyst system exhibits improved stability and, if appropriate, improved catalyst activity.

SUMMARY OF THE INVENTION

Accordingly, a major object of the present invention is the provision of an improved process for the linear dicarbonylation of difunctionalized butenes in the presence of a catalytically effective amount of palladium and of a quaternary onium chloride of a Group VB element of the Periodic Table selected from between nitrogen and phosphorus, such element being tetracoordinated to carbon atoms, with the proviso that the nitrogen atom may be coordinated to two pentavalent phosphorus atoms, in liquid phase, at an elevated temperature and at a pressure above atmospheric pressure, and further wherein (a) the palladium is introduced, at least partially, in the form of palladium in the zero oxidation state and (b) the reaction is also carried out in the presence of at least one source of hydrogen chloride.

DETAILED DESCRIPTION OF THE PREFERRED EMBODIMENTS OF THE INVENTION

More particularly according to the present invention, as indicated above, one of the starting materials employed in the subject process is at least one butene which is difunctionalized, namely, disubstituted by hydroxyl, alkoxy or acyloxy radicals, whether 2-butene disubstituted in positions 1 and 4 or 3-butene disubstituted in positions 1 and 2. These difunctionalized butenes may be represented by either of the formulae below:

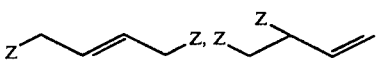

in which Z is an —OH, —OR or —O—(CO)—R radical, wherein R is a linear, branched or cyclic alkyl radical having from 1 to 12 carbon atoms and preferably from 1 to 4 carbon atoms.

Exemplary difunctionalized butenes according to the present invention include:

(i) 2-Butene-1,4-diol, 3-butene-1,2-diol and mixtures thereof;

(ii) 1,4-Dimethoxy-2-butene, 1,2-dimethoxy-3-butene and mixtures thereof;

(iii) 1,4-Diethoxy-2-butene, 1,2-diethoxy-3-butene and mixtures thereof;

(iv) 1,4-Diacetoxy-2-butene, 1,2-diacetoxy-3-butene and mixtures thereof.

Although, in principle, a mixture of various starting materials may be selected from among the above disubstituted butenes, in practice it has proved more advantageous to employ mixtures of diols, mixtures of dialkoxybutenes, or mixtures of diacyloxybutenes.

Indeed, it has now been found that the selectivity for a linear dicarbonylation product is substantially the same whether the starting material is a 2-butene disubstituted in positions 1 and 4 or a 3-butene disubstituted in positions 1 and 2, for a given type of substituent.

3-Hexene-1,6-dioic acid will be obtained as the predominant compound from butenediol(s) and carbon monoxide via the process according to the invention.

The corresponding alkyl 3-hexenedioate will be obtained as the predominant final compound from dialkoxybutene(s) and carbon monoxide via the process according to the invention.

3-Hexene-1,6-dioic acid will be obtained as the predominant final compound from diacyloxybutene(s), carbon monoxide and water via the process according to the invention.

3-Hexene-1,6-dioic acid and the alkyl esters thereof, in proportions which can vary according to the reaction conditions, will be obtained as the predominant final compounds from diacyloxybutene(s), carbon monoxide and an alcanol via the process according to the invention.

It is also an essential characteristic of the present invention that the dicarbonylation reaction be carried out in the presence of palladium, employed at least partially in the form of palladium in the zero oxidation state.

To accomplish this, it is possible to use finely divided metallic palladium or metallic palladium deposited onto a support such as silicas, aluminas, silicoaluminas, zirconia, quartz, clays and active carbons.

Palladium deposited on active carbon is more particularly suitable according to the present invention.

The amount of palladium deposited on the support can vary over wide limits. An amount ranging from 1% to 10% by weight offers an acceptable compromise between the economic constraints and the efficiency which is required.

The dicarbonylation is also carried out in the presence of a quaternary onium chloride of a Group VB element of the Periodic Table selected from between nitrogen and phosphorus, said element being tetracoordinated to carbon atoms, with the proviso that the nitrogen atom may be coordinated to two pentavalent phosphorus atoms.

The quaternary onium cations indicated above are well known to this art; compare, for example, European Application EP-A-0,347,340, hereby expressly incorporated by reference.

A quaternary onium chloride is preferably used, in which the cation corresponds to one of the formulae (I) and (II) below:

in which A is a nitrogen or phosphorus atom; the radicals $R_1$, $R_2$, $R_3$ and $R_4$, which may be identical or different, are each a linear or branched chain alkyl radical having from 1 to 8 carbon atoms, an aryl radical having from 6 to 10 carbon atoms, optionally substituted by one or more alkyl radicals having 1 to 4 carbon atoms; and the radicals $R_5$, $R_6$, $R_7$ and $R_8$, which may be identical or different, are each a linear or branched chain alkyl radical having from 1 to 4 carbon atoms, with the proviso that the radicals $R_7$ and $R_8$ may together form an alkylene radical having from 3 to 6 carbon atoms, and the radicals $R_6$ and $R_7$ or $R_6$ and $R_8$ may together form an alkylene, alkenylene or alkadienylene radical having 4 carbon atoms and constituting a nitrogenous heterocyclic ring with N.

A quaternary phosphonium chloride whose cation corresponds to the formula (I) above is advantageously used.

Tetrabutylphosphonium chloride, which is readily available and particularly effective, is more especially preferred.

The onium cation/palladium molar ratio advantageously ranges from 0.5 to 150, the upper limit of this ratio being dictated only by economic considerations. Said molar ratio preferably ranges from 5 to 150.

In another essential embodiment of the present invention, the dicarbonylation is carried out in the presence of at least one source of hydrogen chloride.

By "source of hydrogen chloride" is intended gaseous HCl, aqueous or organic solutions of HCl and organic chlorides capable of releasing HCl under the reaction conditions.

Among the organic chlorides, the amine hydrochlorides are advantageously used, which are easy to handle and which, when it is desired to prepare predominantly alkyl esters of 3-hexene-1,6-dioic acid, do not form an additional amount of said acid.

More specifically, the amine hydrochloride is characteristically derived from an amine corresponding to any one of the formulae (III) to (VI) below:

-continued

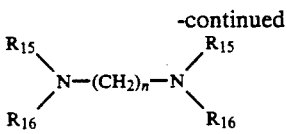
(V)

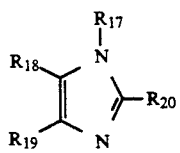
(VI)

in which $R_9$ to $R_{11}$, which may be identical or different, are each a hydrogen atom, a linear or branched chain alkyl radical having from 1 to 16 carbon atoms, optionally substituted by a phenyl, hydroxyl, halo, nitro, alkoxy or alkoxycarbonyl radical, a linear or branched chain alkenyl radical having from 2 to 12 carbon atoms, preferably from 4 to 8 carbon atoms, an aryl radical having from 6 to 10 carbon atoms, optionally substituted by one or more alkyl radicals having from 1 to 4 carbon atoms, or by alkoxy or alkoxycarbonyl radicals or halogen atoms, with the proviso that two of said radicals $R_9$ to $R_{11}$ may altogether form a linear or branched chain alkylene, alkenylene or alkadienylene radical having from 3 to 6 carbon atoms; $R_{12}$ to $R_{14}$, which may be identical or different, are each a linear or branched chain alkyl radical having from 1 to 4 carbon atoms, with the proviso that the radicals $R_{13}$ and $R_{14}$ may together form an alkylene radical having from 3 to 6 carbon atoms and the radicals $R_{12}$ and $R_{13}$ (or $R_{12}$ and $R_{14}$) may together form an alkylene, alkenylene or alkadienylene radical having 4 carbon atoms and defining a nitrogenous heterocyclic ring with N; $R_{15}$ and $R_{16}$, which may be identical or different, are each a hydrogen atom, a linear or branched chain alkyl radical having from 1 to 4 carbon atoms, a linear or branched chain alkenyl radical having from 2 to 12 carbon atoms, preferably from 4 to 8 carbon atoms; n is an integer ranging from 1 to 6, inclusive; $R_{17}$ is as defined above for $R_9$ to $R_{11}$; $R_{18}$ to $R_{20}$, which may be identical or different, are each a hydrogen atom, a linear or branched chain alkyl radical having from 1 to 16 carbon atoms, optionally substituted by a phenyl, hydroxyl, halo, nitro, alkoxy or alkoxycarbonyl radical, or a linear or branched chain alkenyl radical having from 2 to 12 carbon atoms, preferably from 4 to 8 carbon atoms.

Exemplary of the amines corresponding to the formula (III) are:
ammonia,
mono-, di- and trimethylamines,
mono-, di- and triethylamines,
mono-, di- and tri-n-propylamines,
mono-, di- and tributylamines,
mono-, di- and triisopropylamines,
mono-, di- and tripentylamines,
mono-, di- and trihexylamines,
mono-, di- and trioctylamines,
mono-, di- and dtridodecylamines,
cyclohexylamine,
aniline,
diphenylamine,
benzylamine,
triethanolamine,
diethylmethylamine,
N,N-dimethylethanolamine,
N,N-diethylaniline,
2,6-diethylaniline,
N,N-diethylcyclohexylamine,
dimethylaminobenzylamine,
N,N-dimethyl-2-chloroethylamine,
pyrrolidine,
2-chloroaniline,
triethylenediamine,
quinuclidine,
1,2,3,4-tetrahydro-i-naphthylamine,
piperazine.

Exemplary of the amines corresponding to the formula (IV) are:
pyridine,
3-methylpyridine,
2-phenylpyridine,
indole,
2-picoline,
diazabicyclo[5.4.0]undec-7-ene,
pyrrole,
1-methylpyrrole,
quinoline,
5,6,7,8-tetrahydroisoquinoline,
pyrimidine.

Exemplary of the amines corresponding to the formula (V) are:
N,N'-diethylethylenediamine,
N,N-diethyl-N'-methylethylenediamine,
N,N'-diethyl-1,3-propanediamine,
N,N,N',N'-tetramethyl-1,4-butanediamine,
N,N,N',N'-tetraethylenediamine.

And exemplary of the amines corresponding to the formula (VI) are:
imidazole,
1-methylimidazole.

A hydrochloride derived from an amine selected from among methylamine, pyridine, methylimidazole, benzylamine, aniline and chloroaniline is advantageously used.

A tertiary amine hydrochloride is preferably employed to avoid the risk of amide formation.

The amount of amine hydrochloride to be used according to the invention can vary over wide limits.

Good results are attained using a quantity of amine hydrochloride such that the hydrochloride/Pd molar ratio ranges from 0.5 to 100 and preferably from 2 to 20.

The dicarbonylation reaction may, of course, be carried out in the absence or in the presence of a solvent exogenic to the reaction system. When it is desired to use organic solvents, it is possible to employ polar and basic aprotic solvents such as N-methyl-2-pyrrolidone, tetramethylurea and N,N-dimethylacetamide, or apolar and nonbasic solvents such as esters, saturated aliphatic or cycloaliphatic hydrocarbons or aromatic hydrocarbons.

When a solvent is used, its quantity represents at least 10% of the reaction volume; good results can be obtained when on the order of 20% to 90% by volume is employed.

The dicarbonylation reaction is generally conducted at a temperature ranging from 50° to 180° C., preferably from 80° to 150°, at a carbon monoxide pressure above or equal to 20 bars and preferably below or equal to 250 bars.

To advantageously carry out the process according to the invention, the carbon monoxide pressure will preferably range from 90 to 180 bars.

Inert gases such as nitrogen, argon or carbon dioxide may be present in addition to the carbon monoxide.

Upon completion of the reaction or of the time allocated thereto, the desired diacid and/or its diester is(are) recovered by any suitable means, for example by extraction and/or distillation.

In order to further illustrate the present invention and the advantages thereof, the following specific examples are given, it being understood that same are intended only as illustrative and in nowise limitative.

EXAMPLES 1 to 5: Control test (a)

The following materials were introduced into a 125-cm$^3$ stainless steel (316 L) autoclave purged beforehand with argon:

(i) 52 mmol of 1,4-dimethoxy-2-butene, (ii) 0.5 mmol of palladium in the form of palladium deposited on active carbon [0.5 g of Pd/C containing 10% (wt) of palladium], (iii) 13.6 mmol of tetrabutylphosphonium chloride (4 g), (iv) 5 mmol of the hydrochloride of the amine indicated in Table I below.

The autoclave was closed hermetically, placed in an agitated oven and connected to the supply of gas under pressure. The reactor was purged cold with carbon monoxide and heated to 120° C. The pressure was then set at 140 bars. After reaction, the autoclave was cooled and degassed.

The reaction mixture was then analyzed by gas phase chromatography.

The particular conditions and the results obtained are reported in Table I below, in which:

t denotes the reaction period at temperature,

H$_3$D (%) denotes the molar amount of methyl 3-hexenedioate formed per 100 moles of 1,4-dimethoxy-2-butene charged, and DC (%) denotes the degree of conversion of the 1,4-dimethoxy-2-butene.

TABLE I

| Example | Amine from which the hydrochloride was derived | t (h) | DC (%) | H$_3$D (%) |
|---|---|---|---|---|
| 1 | chloroaniline | 2.8 | 100 | 73 |
| 2 | aniline | 2.3 | 100 | 69 |
| 3 | pyridine | 3.5 | 100 | 86 |
| 4 | methylimidazole | 3.0 | 100 | 86 |
| 5 | benzylamine | 2.4 | 100 | 90 |
| a | none | 1.5 | 96 | 36 |

Control Tests (b) to (d)

A series of tests was carried out in the autoclave by following the procedure described above, on a charge containing: (i) 35 mmol of 1,4-dimethoxy-2-butene, (ii) 0.5 mmol of palladium introduced in the form of palladium deposited on active carbon (10 wt % of palladium), (iii) 18.5 mmol of pyridine hydrochloride.

No formation of dicarbonylation product was detected at 140 bars and under the particular conditions reported in Table II below:

TABLE II

| Test | T(°C.) | t(h) |
|---|---|---|
| b | 120 | 0.75 |
| c | 140 | 2 |
| d | 150 | 1 |

EXAMPLE 6

A reaction was carried out in the autoclave following the procedure described above on a charge containing:

(i) 34 mmol of 1,2-dimethoxy-3-butene, (ii) 0.5 mmol of palladium in the form of palladium deposited on active carbon [0.5 g of Pd/C containing 10% (wt) of Pd], (iii) 13.6 mmol of tetrabutylphosphonium chloride (4 g), (iv) 5 mmol of pyridine hydrochloride.

After 3 hours of reaction at 120° C. and 140 bars of pressure, the autoclave was cooled and degassed.

The reaction mixture was analyzed by high performance liquid chromatography and gas phase chromatography; it was then esterified with methanol at reflux in the presence of trace amounts of sulfuric acid, before being re-analyzed by gas phase chromatography.

The results obtained were the following:

Degree of conversion of dimethoxybutene: 100%. Before esterification, the following products were determined (in moles per 100 moles of dimethoxybutene charged):

(a) Monomethyl ester of 3-hexene-1,6-dioic acid=16%, (b) Methyl 3-hexenedioate=66%.

After esterification, the following compound was determined:

(c) Methyl 3-hexenedioate=77%.

EXAMPLE 7

A reaction was carried out in the autoclave following the procedure described above on a charge containing:

(i) 35 mmol of 1,2-diacetoxy-3-butene, (ii) 0.5 mmol of palladium in the form of palladium deposited on active carbon [0.5 g of Pd/C containing 10% (wt) of Pd], (iii) 13.6 mmol of tetrabutylphosphonium chloride (4 g), (iv) 5 mmol of pyridine hydrochloride.

After 2.5 hours of reaction at 120° C. and 140 bars of pressure, the autoclave was cooled and degassed.

The reaction mixture was analyzed before and after esterification as described in Example 6.

The results obtained were as follows:

Degree of conversion of diacetoxybutene: 100%. Before esterification, the following products were determined (in moles per 100 moles of diacetoxybutene charged):

(a) 3-hexene-1,6-dioic acid=9%, (b) monomethyl ester of 3-hexene-1,6-dioic acid=24%, (c) methyl 3-hexenedioate=41%.

After esterification, the following compound was determined:

(d) methyl 3-hexenedioate=66%.

EXAMPLE 8

A reaction was carried out in the autoclave following the procedure described above on a charge containing:

(i) 36 mmol of 1,4-diacetoxy-2-butene, (ii) 72 mmol of water, (iii) 0.5 mmol of palladium in the form of palladium deposited on active carbon [0.5 g of Pd/C containing 5% (wt) of Pd), (iv) 13.6 mmol of tetrabutylphosphonium chloride (4 g), (v) 5 mmol of pyridine hydrochloride.

After 3 hours of reaction at 120° C. and 140 bars of pressure, the autoclave was cooled and degassed.

The reaction mixture was analyzed before and after esterification as described in Example 6.

The results obtained were as follows:

Degree of conversion of diacetoxybutene: 100%.
Before esterification:
(a) 3-hexene-1,6-dioic acid=47%,
(b) monomethyl ester of 3-hexene-1,6-dioic acid=6%,
(c) methyl 3-hexenedioate=0%.
After esterification:
(d) methyl 3-hexenedioate=48%.

EXAMPLE 9

A reaction was carried out in the autoclave following the procedure described above on a charge containing:
(i) 39 mmol of 1,4-butenediol,
(ii) 70 mmol of methanol,
(iii) 0.5 mmol of palladium in the form of palladium deposited on active carbon [0.5 g of Pd/C containing 0.5% (wt) of Pd],
(iv) 13.6 mmol of tetrabutylphosphonium chloride (4 g),
(v) 5 mmol of pyridine hydrochloride. After 2 hours of reaction at 120° C. and 140 bars of pressure, the autoclave was cooled and degassed.

The reaction mixture was esterified and then analyzed as described previously.

The results obtained were as follows:

Degree of conversion of 1,4-butenediol 100%. After esterification:
(a) methyl 3-hexenedioate=50%,
(b) 3-hexene-1,6-dioic acid=12%.

EXAMPLES 10 to 15

A series of tests was carried out in the autoclave following the procedure described above on a charge containing:
(i) 53 mmol of 1,4-dimethoxy-2-butene,
(ii) 0.5 mmol of palladium introduced in the form of palladium deposited on active carbon (10 wt %),
(iii) tetrabutylphosphonium chloride in varying amounts, indicated in Table III below:
(i) 5 mmol of methylamine hydrochloride,
(ii) dimethyl adipate: q.s. 50 ml unless otherwise indicated.

The particular conditions and the results obtained at 120° C. and 140 bars of pressure are reported in Table III below. The conventions employed therein are the same as in Table I.

TABLE III

| Example | PBu$_4$Cl (mmol) | t (h) | DC % | H$_3$D (%) |
|---|---|---|---|---|
| 10 | 3.4 | 4 | 99.5 | 52 |
| 11 | 6.8 | 4 | 100 | 70 |
| 12 | 13.6 | 3 | 99 | 72 |
| 13 | 27 | 4 | 100 | 68 |
| 14 (*) | 6.8 | 4 | 100 | 81 |
| 15 (**) | 6.8 | 3 | 100 | 60 |

(*) test carried out using a total volume of 25 cm$^3$ and a water content of 0.2 mmol. The formation of a small amount (2%) of the monomethyl ester of 3-hexenedioic acid was observed.
(**) test carried out using a total volume of 25 cm$^3$ and a water content of 6 mmol. The formation of a small amount (1%) of the monomethyl ester of 3-hexenedioic acid was observed.

EXAMPLE 16

A reaction was carried out in the autoclave following the procedure described above on a charge containing:
(i) 35 mmol of 1,4-dimethoxy-2-butene,
(ii) 0.5 mmol of palladium introduced in the form of palladium deposited on active carbon (10 wt %),
13.6 mmol of tetrabutylphosphonium chloride,
(iv) 5 mmol of pyridine hydrochloride,
(v) 10 ml of pentane.

The results obtained after 3.3 hours of reaction at 120° C. and 1,450 bars of pressure were as follows:

DC (%)=100,

H$_3$D (%)=71,

Monomethyl ester of 3-hexene-1,6-dioic acid (%)=24,
3-Hexene-1,6-dioic acid=3.

EXAMPLES 17 to 21

A series of tests was carried out in the autoclave following the procedure described above, on a charge containing:
(i) 17.8 mmol of 1,2-dimethoxy-3-butene,
(ii) 0.5 mmol of palladium introduced in the form of palladium deposited on active carbon containing 10% (wt) of Pd (unless otherwise indicated),
(iii) 14 mmol of tetrabutylphosphonium chloride,
(iv) 2 mmol of hydrochloric acid in aqueous solution (10 N) (unless otherwise indicated),
(v) a hydrocarbon solvent, the nature and amount of which are reported in Table IV below.

Upon completion of the reaction, the reaction mixture was determined by gas phase chromatography.

The particular conditions and the results obtained at 120° C. and 140 bars of pressure are reported in Table IV below, in which:
t(h) denotes the reaction period expressed in hours,
H$_3$D (%) is as defined above,
MME (%) denotes the molar amount of monomethyl ester of 3-hexene-1,6-dioic acid per 100 moles of 1,2-dimethoxy-3-butene charged,
ACID (%) denotes the molar amount of 3-hexene-1,6-dioic acid per 100 moles of 1,2-dimethoxy-3-butene charged.

TABLE IV

| Example | Pd mmol | Solvent nature | ml | t (h) | DC (%) | H$_3$D (%) | MME (%) | ACID (%) |
|---|---|---|---|---|---|---|---|---|
| 17 (*) | 0.5 | cyclohexane | 30 | 1 | 98 | 14 | 12 | 47 |
| 18 | 0.5 | cyclohexane | 30 | 1 | 100 | 32 | 36 | 27 |
| 19 | 0.5 | pentane | 60 | 1.4 | 94 | 26 | 24 | 33 |
| 20 | 0.2 | cyclohexane | 30 | 2 | 99 | 40 | 35 | 15 |
| 21 (**) | 0.25 | pentane | 60 | 1.7 | 76 | 14 | 12 | 32 |

(*) test carried out using 5 mmol of HCl (10 N)
(**) test carried out using 7 mmol of PBu$_4$Cl.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the linear dicarbonylation of a difunctionalized butene, comprising reacting such butene with carbon monoxide at a temperature of 50° C. to 180° C. under superatmospheric pressure, in the presence of at least one source of hydrogen chloride, a catalytically effective amount of palladium, at least a portion of which palladium being in the zero oxidation state, and a quaternary onium chloride of nitrogen or phosphorus, said nitrogen or phosphorus atom being tetracoordinated to carbon atoms, with the proviso that the nitrogen atom may be coordinated to two pentavalent phosphorus atoms.

2. The process as defined in claim 1, said palladium comprising metallic palladium deposited onto a support substrate therefor.

3. The process as defined in claim 2, said support substrate is active carbon.

4. The process as defined in claim 1, said at least one source of hydrogen chloride is gaseous HCl, an aqueous solution of HCl, an organic solution of HCl or an organic chloride capable of releasing HCl under the conditions of the reaction.

5. The process as defined by claim 1, said at least one source of hydrogen chloride is the hydrochloride of an amine corresponding to any one of the following formulae (III) to (VI):

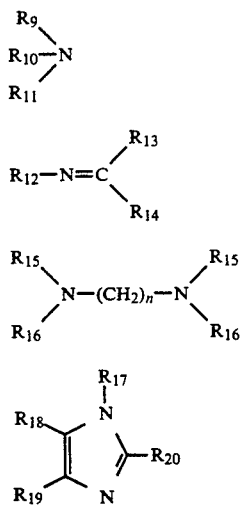

in which $R_9$ to $R_{11}$, which may be identical or different, are each a hydrogen atom, a linear or branched chain alkyl radical having from 1 to 16 carbon atoms, optionally substituted by a phenyl, hydroxyl, halo, nitro, alkoxy or alkoxycarbonyl radical, a linear or branched chain alkenyl radical having from 2 to 12 carbon atoms, an aryl radical having from 6 to 10 carbon atoms, optionally substituted by one or more alkyl radicals having from 1 to 4 carbon atoms or by alkoxy of alkoxycarbonyl or a halogen atom, with the proviso that two of said radicals $R_9$ to $R_{11}$ may together form a linear or branched chain alkylene, alkenylene or alkadienylene radical having from 3 to 6 carbon atoms; $R_{12}$ to $R_{14}$, which may be identical or different, are each a linear or branched chain alkyl radical having from 1 to 4 carbon atoms, with the proviso that the radicals $R_{13}$ and $R_{14}$ may together form an alkylene radical having from 3 to 6 carbon atoms, and the radicals $R_{12}$ and $R_{13}$ or $R_{12}$ and $R_{14}$ may together form an alkylene, alkenylene or alkadienylene radical having 4 carbon atoms and constituting a nitrogenous heterocyclic ring member with N; $R_{15}$ and $R_{16}$, which may be identical or different, are each a hydrogen atom, a linear or branched chain alkyl radical having from 1 to 4 carbon atoms, a linear or branched chain alkenyl radical having from 2 to 12 carbon atoms; n is an integer ranging from 1 to 6; $R_{17}$ is $R_9$ to $R_{11}$ as defined above; and $R_{18}$ to $R_{20}$, which may be identical or different, are each a hydrogen atom, a linear or branched chain alkyl radical having from 1 to 16 carbon atoms, optionally substituted by a phenyl, hydroxyl, halo, nitro, alkoxy or alkoxycarbonyl radical, or a linear or branched chain alkenyl radical having from 2 to 12 carbon atoms.

6. The process as defined by claim 5, said hydrochloride being of methylamine, pyridine, methylimidazole, benzylamine, aniline or chloroaniline.

7. The process as defined by claim 5, said hydrochloride being of a tertiary amine.

8. The process as defined by claim 1, carried out in a hydrocarbon reaction solvent.

9. The process as defined by claim 5, wherein the amine hydrochloride/Pd molar ratio ranges from 0.5 to 100.

10. The process as defined by claim 1, wherein the concentration of palladium in the medium of reaction ranges from $10^{-3}$ to 1 mol/l.

11. The process as defined by claim 1, wherein the quaternary onium chloride/Pd molar ratio ranges from 0.5 to 150.

12. The process as defined by claim 1, said quaternary onium chloride is tetrabutylphosphonium chloride.

13. The process as defined by claim 1, carried out under a pressure of at least 20 bars.

14. The process as defined by claim 13, carried out under a pressure ranging from 90 to 180 bars.

15. The process as defined by claim 1, the medium of reaction also including at least one alcohol.

16. The process as defined by claim 1, said difunctionalized butene 2-butene-1,4-diol, 3-butene-1,2-diol, or mixture thereof.

17. The process as defined by claim 1, said difunctionalized butene is 1,4-dimethoxy-2-butene, 1,2-dimethoxy-3-butene, or mixture thereof.

18. The process as defined by claim 1, said difunctionalized butene is 1,4-diethoxy-2-butene, 1,2-diethoxy-3-butene, or mixture thereof.

19. The process as defined by claim 1, said difunctionalized butene is 1,4-diacetoxy-2-butene, 1,2-diacetoxy-3-butene, or mixture thereof.

* * * * *